(12) United States Patent
Nair et al.

(10) Patent No.: US 7,973,195 B2
(45) Date of Patent: Jul. 5, 2011

(54) PROCESS FOR UNSATURATED QUATERNARY AMMONIUM SALT

(75) Inventors: Mohan Nair, Oradell, NJ (US); C. Joseph Calbick, Weston, CT (US)

(73) Assignee: Kemira Oyj (FI)

( * ) Notice: Subject to any disclaimer, the term of this patent is extended or adjusted under 35 U.S.C. 154(b) by 155 days.

(21) Appl. No.: 12/507,122

(22) Filed: Jul. 22, 2009

(65) Prior Publication Data

US 2011/0021808 A1    Jan. 27, 2011

(51) Int. Cl.
*C07C 69/52* (2006.01)
(52) U.S. Cl. ...................................................... 560/222
(58) Field of Classification Search .................. None
See application file for complete search history.

(56) References Cited

U.S. PATENT DOCUMENTS

| | | | |
|---|---|---|---|
| 4,239,876 A | 12/1980 | Arndt et al. | |
| 4,520,210 A | 5/1985 | Schneider et al. | |
| 4,745,214 A * | 5/1988 | Hess et al. | 560/222 |
| 5,260,480 A | 11/1993 | Lacroix et al. | |
| 5,912,383 A | 6/1999 | Riondel et al. | |
| 6,521,782 B1 | 2/2003 | Riondel et al. | |
| 6,683,203 B2 | 1/2004 | Druzkowski et al. | |
| 7,151,190 B1 | 12/2006 | Riondel et al. | |
| 7,183,434 B2 | 2/2007 | Baan et al. | |

FOREIGN PATENT DOCUMENTS

WO    0043348    7/2000

OTHER PUBLICATIONS

EP 1104400 B1; published Jun. 6, 2001; Alain et al; "Method for Making Aqueous Solutions of Unsaturated Quaternary Ammonium Salts"; Machine Translation; 3 pages.
EP 428970 B1; published May 29, 1991; Dipl-ing et al.; "Process for Preparing Aqueous Solutions or Suspensions of Quaternization Products of Tertiary Aminoalkylesters or Tertiary Aminoalkylamides of Acrylic or Methacrylic Acid, for Instance of Dimethylaminoethyl-Acrylate-Methochloride"; Machine Translation; 2 pages.
JP 01-249749; published Oct. 5, 1989; Yasushi et al.; "Production of Unsaturated Quaternary Ammonium Salt"; English Abstract Only; 1 page.
JP 02-129156 A; Published May 17, 1990; Akimoto et al.; "Preparation of Cationic Monomer and Polymer Thereof"; Machine Translation; 14 pages.
JP 02-212457; Published Aug. 23, 1990; Naoki, et al.; "Production of Unsaturated Quaternary Ammonium Salt"; English Abstract only; 1 page.
JP 02-243661; Published Sep. 27, 1990; Tetsuya et al.; "Production of Unsaturated Quaternary Ammonium Salt"; English Abstract only; 1 page.
JP 02-670699 B2; Published Sep. 27, 1990; Uchida Seiji; "Manufacturing Method of Unsaturated Quaternary Ammonium Salt"; Machine Translation; 9 pages.
JP 02-773049 B2; Publication Date of Translation Jun. 6, 1991; Rakurowa et al.; "Quaternary Chloride Method"; Machine Translation; 12 pages.
JP 03-041058 A; Published Feb. 21, 1991; Toshiro et al.; "Production of Unsaturated Quaternary Ammonium Salt"; Machine Translation; 8 pages.
JP 03-135945 A; Published Jun. 10, 1991; Toshiro et al.; "Quaternary Ammonium Salt and Production Thereof"; Machine Translation; 13 pages.
JP 04-095053 A; Published Mar. 27, 1992; Nanba Hiroyuki; "Production of Aqueous Solution of Unsaturated Quaternary Ammonium Salt"; Machine Translation; 10 pages.
JP 04-124164 A; Published Apr. 24, 1992; Nanba Hiroyuki; "Production of Acueous Solution of Unsaturated Quaternary Ammonium Salt"; Machine Translation; 13 pages.
JP 04-210664 A; Published Jul. 31, 1992; Kenji et al.; "Production of Unsaturated Quaternary Ammonium Salt"; Machine Translation; 12 pages.
JP 04-217648 A; Published Aug. 7, 1992; Kenji et al.; "Production of Unsaturated Quaternary Ammonium Salt"; Machine Translation; 10 pages.
JP 05-2027712 A; Published Mar. 2, 1977; Masaya et al.; "Process for Preperation of Unsaturated Quaternary Ammonium Salt"; Machine Translation; 6 pages.
JP 06-032768; Published Feb. 8, 1994; Yoshihide, et al.; "Production of Unsaturated Quaternary Ammonium Salt"; English Abstract only; 1 page.
JP 07-206790; Published Aug. 8, 1995; Kenji et al.; "Production of Unsaturated Quaternary Ammonium Salt"; English Abstract only; 1 page.
JP 07-206790; Published Aug. 8, 1995; Kenji et al.; "Production of Unsaturated Quaternary Ammonium Salt"; Machine Translation; 6 pages.
JP 2001-172235; Published Jun. 26, 2001; Yoshihide, et al.; "Method for Producing Dimethylaminoethyl Acrylate"; English Abstract only; 1 page.
JP 2003-342244; Published Dec. 3, 2003; Takeshi et al.; "Method for Producing Quaternary Salt of Dialkylaminoalkyl (Meth) Acrylate"; Machine Translation; 10 pages.

(Continued)

*Primary Examiner* — Paul A Zucker
(74) *Attorney, Agent, or Firm* — Cantor Colburn LLP

(57) ABSTRACT

An unsaturated quaternary ammonium salt is produced by a process that includes reacting methyl chloride in a first vessel with a stoichiometric excess of an unsaturated tertiary amine in the presence of water to form a reaction mixture that includes the unsaturated quaternary ammonium salt and residual unsaturated tertiary amine. The reaction mixture is transferred to a second vessel and phase separated to yield a first fraction in which the unsaturated quaternary ammonium salt is concentrated, and a second fraction in which the residual unsaturated tertiary amine is concentrated. At least a portion of the second fraction is recycled from the second vessel to the first vessel for use in the reaction with methyl chloride. The process, which is preferably operated continuously, allows the use of reduced reaction pressures compared to processes utilizing a stoichiometric excess of methyl chloride, and it also reduces or eliminates the problems associated with recycling methyl chloride and removing methyl chloride from the unsaturated quaternary ammonium salt product.

12 Claims, 1 Drawing Sheet

OTHER PUBLICATIONS

JP 2004-115473 A; Published Apr. 15, 2004; Endo, et al.; "Manufacturing Method of Unsaturated Quaternary Ammonium Salt Group or its Salt"; Machine Translation; 24 pages.

JP 2004-155669; Published Jun. 3, 2004; Takeshi et al.; "Method for Producing Dialkylaminoalkyl (Meth)Acrylate Quaternary Salt"; Machine Translation; 11 pages.

JP 2004-168676 A; Published Jun. 17, 2004; Fukui et al.; "Manufacturing Method of Unsaturated Quaternary Ammonium Salt"; Machine Translation; 16 pages.

JP 2005-075816 A; Published Mar. 24, 2005; Fukui et al.; "Production Method of Unsaturated Quaternary Ammonium Salt Group or Its Salt"; Machine Translation; 20 pages.

* cited by examiner

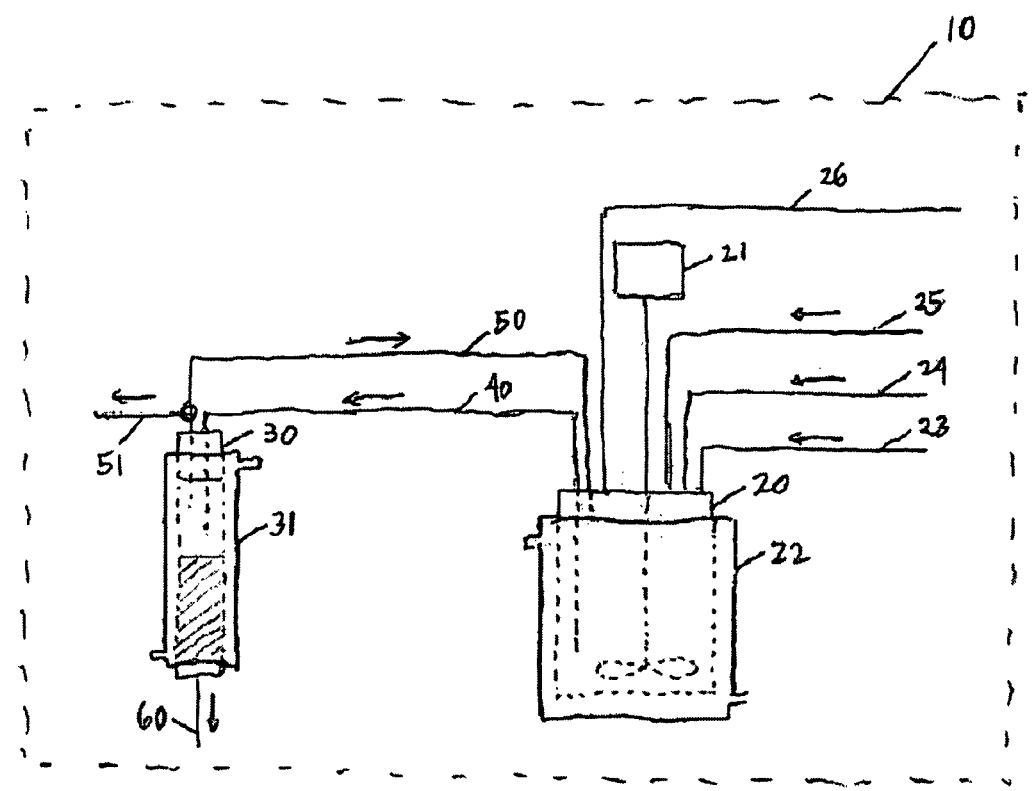
FIG.

PROCESS FOR UNSATURATED QUATERNARY AMMONIUM SALT

BACKGROUND OF THE INVENTION

Unsaturated quaternary ammonium salts, such as acryloyloxyethyl trimethylammonium chloride (Cl⁻(CH₃)₃N⁺CH₂CH₂OC(O)CH=CH₂; CAS Reg. No. 44992-01-0), are widely used as co-monomers in the synthesis of flocculant polymers for water treatment. The unsaturated quaternary ammonium salts are typically prepared by alkylation of the corresponding tertiary amine with an alkyl halide, such as methyl chloride. The literature includes many specific procedures for carrying out these reactions. In these procedures, methyl chloride is typically used in molar excess relative to the tertiary amine. See, for example, U.S. Pat. No. 4,520,210 to Schneider et al., U.S. Pat. No. 4,745,214 to Hess et al., U.S. Pat. No. 5,260,480 to Lacroix et al., U.S. Pat. No. 5,912,383 to Riondel, U.S. Pat. No. 6,521,782 to Riondel et al., U.S. Pat. No. 6,683,203 B2 to Druzkowski et al., U.S. Pat. No. 7,151,190 of Riondel, and U.S. Pat. No. 7,183,434 B2 to Baan et al.; Japanese Patent Application Publication Nos. JP 01-249749 A of Inagaki et al., JP 02-212457 A of Iwasaki et al., JP 06-032768 of Masuda et al.; European Patent Application Publication No. EP428970 A1 of Ascherl et al.; and International Patent Application Publication No. WO 00/43348 of Riondel et al. Reactions run in the presence of a stoichiometric excess of methyl chloride generally produce a high conversion of the tertiary amine and therefore largely avoid problems associated with separating the product unsaturated quaternary ammonium salt from residual tertiary amine reactant. However, such reactions have disadvantages that include requiring relatively high reaction pressures (to produce a high solution concentration of methyl chloride, which is a gas at ambient conditions), requiring special procedures and equipment for recycling excess methyl chloride, and requiring special procedures and equipment to maintain a substantial oxygen concentration while removing excess methyl chloride from the product solution (oxygen inhibits the undesired polymerization of the unsaturated quaternary ammonium salt). It would therefore be desirable to have a method of producing unsaturated quaternary ammonium salts that avoids difficult separations of the unsaturated quaternary ammonium salt from the unsaturated tertiary amine while reducing or eliminating the problems associated with handling excess methyl chloride.

BRIEF DESCRIPTION OF THE INVENTION

The above-described drawbacks are alleviated by a process for producing an unsaturated quaternary ammonium salt, comprising: reacting methyl chloride in a first vessel with a stoichiometric excess of an unsaturated tertiary amine in the presence of water to form a reaction mixture comprising the unsaturated quaternary ammonium salt and residual unsaturated tertiary amine; transferring a portion of the reaction mixture to a second vessel; phase separating the portion of the reaction mixture in the second vessel to yield a first fraction comprising the unsaturated quaternary ammonium salt and water, and a second fraction comprising the residual unsaturated tertiary amine; withdrawing a portion of the first fraction from the second vessel to recover the quaternary ammonium salt product; and recycling a portion of the second fraction from the second vessel to the first vessel for use in said reacting methyl chloride with a stoichiometric excess of unsaturated tertiary amine; wherein the unsaturated tertiary amine has the formula

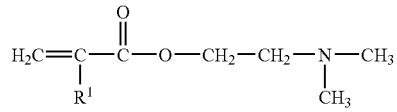

wherein R¹ is hydrogen or methyl; and wherein the unsaturated quaternary ammonium salt has the formula

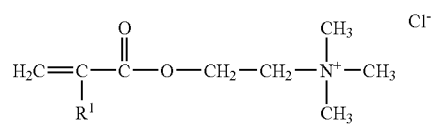

wherein R¹ is hydrogen or methyl.

The present inventors have discovered that it is possible to efficiently produce unsaturated quaternary ammonium salts using a process in which the unsaturated tertiary amine reactant is used in stoichiometric excess relative to methyl chloride, and product unsaturated quaternary ammonium salt and excess unsaturated tertiary amine are phase separated in a second (e.g., decanter) vessel from which product quaternary ammonium salt is withdrawn and excess unsaturated tertiary amine is recycled for use in the reaction with methyl chloride. The present process has several advantages over prior art processes, including the ability to operate at relatively low reaction pressures, elimination of the need to recycle gaseous methyl chloride, and reduction or elimination of the need to remove methyl chloride from the unsaturated quaternary ammonium salt product. At least two aspects of the present process are particularly surprising. First, given that the unsaturated tertiary amine and unsaturated quaternary ammonium salt are both water soluble, it is surprising that the product unsaturated quaternary ammonium salt could efficiently be phase separated from excess unsaturated tertiary amine. As shown in the working examples, this appears to be true only for the relatively narrow class of unsaturated tertiary amine structures recited in the claims below. Second, it is surprising that running the reaction in the presence of excess tertiary amine did not exacerbate the known problem of base-catalyzed product hydrolysis under the reaction conditions. Operating at elevated temperatures and short reactor residence times appears to minimize hydrolysis levels to acceptable levels.

BRIEF DESCRIPTION OF THE DRAWINGS

The FIGURE depicts an apparatus for conducting the process.

DETAILED DESCRIPTION OF THE INVENTION

The following abbreviations are used herein:
AETAC=acryloyloxyethyl trimethylammonium chloride, CAS Reg. No. 44992-01-0
CSTR=continuous stirred tank reactor
DMAEA=2-(dimethylamino)ethyl acrylate, CAS Reg. No. 2439-35-2
DMAEMA=2-(dimethylamino)ethyl methacrylate, CAS Reg. No. 2867-42-2
MAETAC=methacryloyloxyethyl trimethylammonium chloride, CAS Reg. No. 5039-78-1

The invention includes a process for producing an unsaturated quaternary ammonium salt, comprising: reacting methyl chloride in a first vessel with a stoichiometric excess of an unsaturated tertiary amine in the presence of water to form a reaction mixture comprising the unsaturated quaternary ammonium salt and residual unsaturated tertiary amine; transferring a portion of the reaction mixture to a second vessel; phase separating the portion of the reaction mixture in the second vessel to yield a first fraction comprising the unsaturated quaternary ammonium salt and water, and a second fraction comprising the residual unsaturated tertiary amine; withdrawing a portion of the first fraction from the second vessel to recover the quaternary ammonium salt product; and recycling a portion of the second fraction from the second vessel to the first vessel for use in said reacting methyl chloride with a stoichiometric excess of unsaturated tertiary amine; wherein the unsaturated tertiary amine has the formula

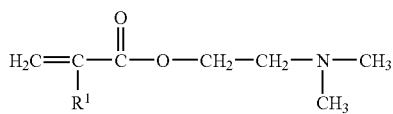

wherein $R^1$ is hydrogen or methyl; and wherein the unsaturated quaternary ammonium salt has the formula

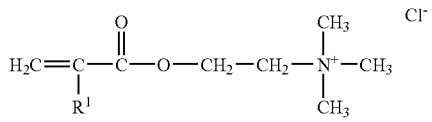

wherein $R^1$ is hydrogen or methyl.

The process is preferably operated continuously in order to maximize the productivity of the apparatus. In this context, "continuous" is used in its conventional sense to mean that reactant streams are constantly introduced to the first vessel (e.g., reactor) and a product stream is constantly withdrawn from the second vessel (e.g., decanter). In a preferred embodiment, all of the steps of reacting, transferring, phase separating, withdrawing, and recycling are conducted continuously. While less efficient than a continuous process, it is also possible to operate the process in batch or semi-batch modes, or to introduce and/or remove process flows in an intermittent rather than a continuous manner.

The reaction of methyl chloride with unsaturated tertiary amine is conducted a stoichiometric excess of an unsaturated tertiary amine. This means that more than one mole of unsaturated tertiary amine is used for each mole of methyl chloride. The molar ratio of unsaturated tertiary amine to methyl chloride is most conveniently determined using inputs to the first vessel. Specifically, when the process is operated continuously, the molar ratio of unsaturated tertiary amine to methyl chloride is the ratio of the moles of methyl chloride added to the first vessel per unit time to the sum of (1) the moles of fresh unsaturated tertiary amine added to the first vessel per unit time, and (2) the moles of unsaturated tertiary amine transferred (recycled) from the second vessel to the first vessel per unit time. In some embodiments, the stoichiometric excess of the unsaturated tertiary amine corresponds to a molar ratio of unsaturated tertiary amine to methyl chloride of 1.05:1 to 5:1, as determined for inputs to the first vessel. The molar ratio can be 1.1:1 to 4:1, or 1.2:1 to 3:1, or 1.3:1 to 2:1.

As explained in the working examples below, the process is useful for a very limited range of unsaturated tertiary amine structures. One such structure is 2-(dimethylamino)ethyl acrylate. Another is 2-(dimethylamino)ethyl methacrylate. These molecules exhibit useful reaction rates with methyl chloride under low pressure conditions, and they also allow efficient phase separation of the unsaturated quaternary ammonium salt product from the residual unsaturated tertiary amine.

In a very specific set of conditions for continuous operation of the process, the first vessel is continuous fed with 6 to 20 weight percent methyl chloride, 18 to 57 weight percent (fresh) unsaturated tertiary amine, 6 to 19 weight percent water, and 3 to 70 weight percent of the recycled portion of the second fraction, wherein all weight percents are based on the total weight of inputs to the first vessel. Within the range of 6 to 20 weight percent, the amount of methyl chloride can be 8 to 15 weight percent. Within the range of 18 to 57 weight percent, the amount of (fresh) unsaturated tertiary amine can be 30 to 50 weight percent. Within the range of 6 to 19 weight percent, the amount of water can be 9 to 15 weight percent, and within the range of 3 to 70 weight percent, the amount of recycled second fraction can be 10 to 50 weight percent. In some embodiments, the reaction is conducted with a first vessel residence time of 0.25 to 3 hours, specifically 0.25 to 2 hours, more specifically 0.5 to 1.5 hours. Shorter or longer times are also possible, depending on the reaction temperature and pressure, among other factors. In some embodiments, the reaction is conducted at a temperature of 30 to 90° C., specifically 40 to 90° C., more specifically 50 to 90° C., still more specifically 60 to 90° C., even more specifically 65 to 85° C., yet more specifically 70 to 85° C. Lower and higher temperatures are also possible, depending on the reaction pressure and reactor residence time, among other factors.

One important advantage of the present process compared to processes operated with excess methyl chloride is that the reaction can be conducted at reduced pressures. In some embodiments, the reaction is conducted at a total (absolute) pressure of 100 to 800 kilopascals, specifically 150 to 600 kilopascals, more specifically 200 to 500 kilopascals, even more specifically 200 to 400 kilopascals. The term "total pressure" refers to the pressure generated by methyl chloride as well as any other gas or vapor present (e.g., oxygen, nitrogen).

There is no particular limitation on the type of equipment used as the first vessel (i.e., the reactor). For example, the first vessel can be a continuous stirred tank reactor or a plug-flow reactor. Use of a continuous stirred tank reactor is presently preferred.

The process includes the step of transferring a portion of the reaction mixture from the first vessel to a second vessel. Transfer can be effected by a pump or similar transfer means. In general, when the process is operated continuously, the transfer rate (e.g., in mass per unit time) of the reaction mixture from the first vessel to the second vessel will be approximately equal to the sum of the transfer rates into the first vessel (i.e., the sum of the methyl chloride addition rate, the fresh unsaturated tertiary amine addition rate, and the recycled second fraction addition rate).

The process includes the step of phase separating the transferred portion of the reaction mixture in the second vessel. The phase separation can occur spontaneously in a decanter or similar vessel, or it can be accelerated by the use of a liquid-liquid centrifuge or similar phase separation apparatus. In some embodiments, the phase separation is conducted at a temperature of −5 to 15° C., specifically 0 to 10° C. The process is preferably conducted in the absence of organic solvent. No solvent is necessary to achieve efficient phase separation in the second vessel of an aqueous phase consisting essentially of water and the unsaturated quaternary ammonium salt, and an organic phase consisting essentially of neat unsaturated tertiary amine. However, it is possible to utilize a non-water-soluble co-solvent in order to dilute unsaturated tertiary amine in the separated organic phase, and use of such a co-solvent can facilitate extraction of organic impurities from the aqueous phase and removal of such impurities from the system via a purge stream corresponding to the portion of the organic phase not recycled to the first vessel.

The phase separation yields a first fraction comprising the unsaturated quaternary ammonium salt and water, and a second fraction comprising the residual unsaturated tertiary amine. The phase separation typically occurs spontaneously under the conditions of the second vessel. The present inventors have observed that the phase separation is a very efficient means of separating the unsaturated quaternary ammonium salt from the unsaturated tertiary amine. This was surprising given the known water solubility of the unsaturated tertiary amine. Specifically, the first fraction can comprise at least 75% of the unsaturated quaternary ammonium salt in the second vessel, and this percentage can also be at least 90%, or at least 95%, or at least 98%, or at least 99%. Similarly, the second fraction can comprise at least 75% of the unsaturated tertiary amine in the second vessel, and this percentage can be at least 90%, or at least 95%, or at least 98%. In some working examples, it was observed that the first fraction contained essentially all of the unsaturated quaternary ammonium salt and less than or equal to 2% of the unsaturated tertiary amine, while the second fraction contained at least 98% of the unsaturated tertiary amine and was essentially free of quaternary ammonium salt.

The process includes the step of recycling a portion of the second (unsaturated tertiary amine-containing) fraction from the second vessel to the first vessel for use in reacting methyl chloride with excess unsaturated tertiary amine. The recycled portion of the second fraction can be, for example, at least 50 weight percent of the second fraction, or at least 60, 70, 80, or 90 weight percent of the second fraction. The amount of the second fraction not recycled to the first vessel is generally discarded from the process as a means of minimizing the build-up of impurities in the unsaturated tertiary amine. Preventing impurity build-up can be important because certain impurities can promoting emulsion formation in the second vessel, thereby interfering with the phase separation of the first and second fractions.

The process includes the step of withdrawing a portion of the first fraction from the second vessel to recover the quaternary ammonium salt product. In general, the rate of withdrawal of the first fraction from the second vessel (e.g., in mass per unit time) is adjusted to maintain a constant mass (or volume) of first fraction in the second vessel.

In a very specific embodiment of the process, the stoichiometric excess of the unsaturated tertiary amine corresponds to a molar ratio of unsaturated tertiary amine to methyl chloride of 1.1:1 to 4:1; said reacting comprises continuously feeding to the first vessel 6 to 20 weight percent methyl chloride, 18 to 57 weight percent (fresh) unsaturated tertiary amine, 6 to 19 weight percent water, and 3 to 70 weight percent of the recycled portion of the second fraction, wherein all weight percents are based on the total weight of inputs to the first vessel; said reacting is conducted with a first vessel residence time of 0.25 to 3 hours; said reacting methyl chloride with an unsaturated tertiary amine is conducted at a temperature of 30 to 90° C.; said reacting is conducted at a (total) pressure of 150 to 600 kilopascals; said separating is conducted at a temperature of −5 to 15° C.; and the first fraction comprises at least 95 percent of the unsaturated quaternary ammonium salt in the second vessel, and the second fraction comprises at least 95 percent of the residual unsaturated tertiary amine in the second vessel.

The invention includes at least the following embodiments.

Embodiment 1

A process for producing an unsaturated quaternary ammonium salt, comprising: reacting methyl chloride in a first vessel with a stoichiometric excess of an unsaturated tertiary amine in the presence of water to form a reaction mixture comprising the unsaturated quaternary ammonium salt and residual unsaturated tertiary amine; transferring a portion of the reaction mixture to a second vessel; phase separating the portion of the reaction mixture in the second vessel to yield a first fraction comprising the unsaturated quaternary ammonium salt and water, and a second fraction comprising the residual unsaturated tertiary amine; withdrawing a portion of the first fraction from the second vessel to recover the quaternary ammonium salt product; and recycling a portion of the second fraction from the second vessel to the first vessel for use in said reacting methyl chloride with a stoichiometric excess of unsaturated tertiary amine; wherein the unsaturated tertiary amine has the formula

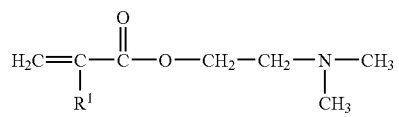

wherein $R^1$ is hydrogen or methyl; and wherein the unsaturated quaternary ammonium salt has the formula

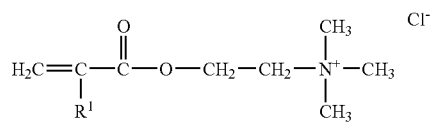

wherein $R^1$ is hydrogen or methyl.

Embodiment 2

The process of embodiment 1, operated continuously.

Embodiment 3

The process of embodiment 1 or 2, wherein the stoichiometric excess of the unsaturated tertiary amine corresponds to a molar ratio of unsaturated tertiary amine to methyl chloride of 1.05:1 to 5:1, as determined for inputs to the first vessel.

Embodiment 4

The process of any of embodiments 1-3, wherein the unsaturated tertiary amine is 2-(dimethylamino)ethyl acrylate.

Embodiment 5

The process of any of embodiments 1-3, wherein the unsaturated tertiary amine is 2-(dimethylamino)ethyl methacrylate.

Embodiment 6

The process of any of embodiments 1-5, wherein said reacting comprises continuously feeding to the first vessel 6 to 20 weight percent methyl chloride, 18 to 57 weight percent unsaturated tertiary amine, 6 to 19 weight percent water, and 3 to 70 weight percent of the recycled portion of the second fraction, wherein all weight percents are based on the total weight of inputs to the first vessel.

Embodiment 7

The process of any of embodiments 1-6, wherein said reacting is conducted with a first vessel residence time of 0.25 to 3 hours.

Embodiment 8

The process of any of embodiments 1-7, wherein said reacting is conducted at a total pressure of 100 to 800 kilopascals.

Embodiment 9

The process of any of embodiments 1-8, wherein said reacting methyl chloride with an unsaturated tertiary amine is conducted at a temperature of 30 to 90° C.

Embodiment 10

The process of any of embodiments 1-9, wherein said phase separating is conducted at a temperature of −5 to 15° C.

Embodiment 11

The process of any of embodiments 1-10, wherein the first fraction comprises at least 95 percent of the unsaturated quaternary ammonium salt in the second vessel, and the second fraction comprises at least 95 percent of the residual unsaturated tertiary amine in the second vessel.

Embodiment 12

The process of embodiment 1, wherein the stoichiometric excess of the unsaturated tertiary amine corresponds to a molar ratio of unsaturated tertiary amine to methyl chloride of 1.1:1 to 4:1; wherein the unsaturated tertiary amine comprises 2-(dimethylamino)ethyl acrylate; wherein said reacting comprises continuously feeding to the first vessel 6 to 20 weight percent methyl chloride, 18 to 57 weight percent unsaturated tertiary amine, 6 to 19 weight percent water, and 3 to 70 weight percent of the recycled portion of the second fraction, wherein all weight percents are based on the total weight of inputs to the first vessel; wherein said reacting is conducted with a first vessel residence time of 0.25 to 3 hours; wherein said reacting methyl chloride with an unsaturated tertiary amine is conducted at a temperature of 30 to 90° C.; wherein said reacting is conducted at a (total) pressure of 150 to 600 kilopascals; wherein said separating is conducted at a temperature of −5 to 15° C.; and wherein the first fraction comprises at least 95 percent of the unsaturated quaternary ammonium salt in the second vessel, and the second fraction comprises at least 95 percent of the residual unsaturated tertiary amine in the second vessel.

The invention is further illustrated by the following non-limiting examples.

Comparative Example 1

This example illustrates a batch process run in the presence of excess methyl chloride.

To a 600-milliliter Inconel Parr pressure reactor was added 200.00 grams of dimethylaminoethyl acrylate (DMAEA) stabilized with 800 parts per million by weight (ppm) of methyl hydroquinone (MEHQ) and 20.36 grams of deionized water (30% of total water). The reactor was sealed and 72.3 grams of methyl chloride (2.5 mole percent excess) was added over 30 minutes while maintaining a temperature of 21° C. The reaction was then heated to 40° C. and the remaining water, 47.45 grams, was added over the course of 30 minutes. The system pressure (absolute pressure) reached 360 kilopascals following water addition. The reaction was maintained at 40° C. for another 3 hours during which time the pressure slowly dropped to a constant value of 190 kilopascals. The reaction was cooled to 25° C. and the pressure was released over the course of 15 minutes while sparging with air to ensure that the dissolved oxygen level remained adequate to inhibit polymerization. The final product had a pH of 7.6 and an acrylic acid level of 0.25%.

General Procedure for Lab-Scale Continuous Reactions

Depicted in the FIGURE is an apparatus for conducting the process. The apparatus 10 includes a continuous stirred tank reactor (CSTR) 20 in which unsaturated tertiary amine is reacted with methyl chloride in the presence of water, and a decanter 30 in which the product unsaturated quaternary ammonium salt is separated from excess unsaturated tertiary amine. The CSTR 20 and decanter 30 are connected to each other by product flow 40, which transfers reaction mixture (including the product quaternary ammonium salt, excess amine reactant, and water) from CSTR 20 to decanter 30, and amine recycle flow 50, which transfers (recycles) amine reactant-containing second fraction from decanter 30 to CSTR 20. Also depicted are reactor stirrer 21, reactor temperature control bath 22, decanter temperature control bath 31, methyl chloride flow 23 (which transfers methyl chloride to CSTR 20), amine flow 24 (which transfers (fresh) amine reactant to CSTR 20), water flow 25 (which transfers water to CSTR 20), vent line 26 (which is connected to a manifold (not shown) containing a pressure transducer, adjustable pressure relief valve, 50 psig rupture disk, and valve to atmospheric pressure), amine purge 51 (through which a portion of excess amine reactant is purged from the system), and product flow 60 (through which the first fraction with product quaternary ammonium salt and water is withdrawn).

In a typical reaction procedure, the CSTR was charged with unsaturated tertiary amine reactant (e.g., DMAEA) and unsaturated quaternary ammonium salt product (e.g., AETAC) in amounts based on the ideal steady state composition for the stoichiometry under examination. The decanter was also charged with unsaturated tertiary amine reactant and unsaturated quaternary ammonium salt product in a weight ratio of about 10:90, respectively.

In order to achieve steady state, it is necessary to match the reaction rate with the reagent feed rates. Controlling the methyl chloride partial pressure was the key to controlling the reaction rate, since methyl chloride partial pressure controls the methyl chloride solution concentration. At a given temperature and reactor amine level, there is therefore a methyl chloride partial pressure required to achieve a reaction rate dictated by the target residence time.

The consequences of not matching the reaction rate with the feed rate are evident in the decanter. If the reaction rate is too slow, amine reactant accumulates to a level higher than is being compensated for by the recycle rate and purge rate, and amine reactant fills the decanter. Conversely, if the reaction rate is too fast, then amine reactant is depleted and the decanter fills with unsaturated quaternary ammonium salt product. At steady state, the unsaturated quaternary ammonium salt product (first fraction) and amine reactant (second fraction) levels in the decanter remain static.

After establishing the target flow rates using a data acquisition system, the system vent was then closed and the reactor charged as rapidly as possible with methyl chloride to a target pressure. The methyl chloride feed rate was then adjusted to match the amine reactant feed rate in a 1:1 mole/mole ratio. During the run, adjustments were made to the methyl chloride partial pressure and/or amine reactant concentration in the reactor to compensate for accumulation or depletion of amine reactant observed in the decanter until steady state was achieved.

Example 1

This example illustrates a continuous process according to the invention. The reaction temperature was 40° C., the reactor residence time was 2.21 hours, and the steady state molar ratio of DMAEA to methyl chloride was 1.6.

A two-liter CSTR was charged with 1033 grams of 80 weight percent aqueous solution of AETAC and 367 grams of DMAEA. The decanter was charged with 295 grams of AETAC and 41 grams of DMAEA. The reactor was heated to 40° C. and the decanter cooled to 5° C., and the system was sealed. The following flow rates were then established: DMAEA, 4.60 grams/minute; $H_2O$, 1.56 grams/minute; CSTR product, 10.54 grams/minute; DMAEA recycle, 2.76 grams/minute; and AETAC decanter product, 7.78 grams/minute.

Methyl chloride was then added at high rate until the system pressure reached an absolute value of 240 kilopascals (corresponding to 20 pounds per square inch gauge (psig)), after which time it was reduced to 1.62 grams/minute (equimolar relative to DMAEA feed). The system pressure ranged between 240 kilopascals (20 psig) and 260 kilopascals (23 psig) for a total of ten hours with the decanter interface being static for the last seven hours. The reactor pressure stabilized at 260 kilopascals (23 psig) and the decanter at 160 kilopascals (8 psig) at steady state. The product was discharged from the decanter to atmospheric pressure without need for degassing dissolved methyl chloride. The acrylic acid level in the resulting product was found to be 0.42 weight percent.

Example 2

This example illustrates a continuous process according to the invention.

The procedure of Example 2 was employed, except that the reaction temperature was 50° C., the reactor residence time was 1.11 hours, and the following flow rates were employed: DMAEA, 9.20 grams/minute; $H_2O$, 3.11 grams/minute; CSTR product, 21.08 grams/minute; DMAEA recycle, 5.52 grams/minute; and AETAC decanter product, 15.56 grams/minute. Methyl chloride was added at high rate until the system pressure reached 240 kilopascals (20 psig), after which time the methyl chloride flow rate was reduced to 3.24 grams/minute (equimolar relative to DMAEA feed). At steady state, the reactor pressure stabilized at 190 kilopascals (13 psig) and the decanter at 115 kilopascals (2 psig). The product was discharged from the decanter to atmospheric pressure without need for degassing dissolved methyl chloride. The acrylic acid level in the resulting product was 0.28%.

Example 3

This example illustrates a continuous process according to the invention.

The procedure of Example 2 was followed, except that the reaction temperature was 60° C., the reactor residence time was 0.74 hour, and the following flow rates were employed: DMAEA, 13.80 grams/minute; $H_2O$, 4.67 grams/minute; CSTR product, 31.62 grams/minute; DMAEA recycle, 8.28 grams/minute; and AETAC decanter product, 23.33 grams/minute. Methyl chloride was added at high rate until the system pressure reached 240 kilopascals (20 psig), after which time the methyl chloride flow rate was reduced to 4.87 grams/minute (equimolar relative to DMAEA feed). At steady state, the reactor pressure stabilized at 210 kilopascals (16 psig) and the decanter at 115 kilopascals (2 psig). The product was discharged from the decanter to atmospheric pressure without need for degassing dissolved methyl chloride. The acrylic acid level in the resulting product was 0.25%.

Examples 4 and 5, Comparative Examples 2-4

These batch reactions demonstrate that subtle changes in amine reactant structure have surprisingly large effects on reaction rate and the ability to phase separate the steady state reaction mixture. Batch reactions were conducted at 75% amine conversion (1.33:1 molar ratio of amine reactant to methyl chloride) on five aminoacrylates to determine whether reaction rates and phase separation rates were suitable for a low pressure continuous process. In order to efficiently operate a continuous process, it is preferred that the reaction be facile at 60° C. and that a good phase separation be obtained between the unsaturated tertiary amine and the aqueous unsaturated quaternary ammonium salt. For the aminoacrylates examined, only dimethylaminoethyl acrylate and dimethylaminoethyl methacrylate satisfied both of these criteria. As noted above, it was surprising that a good phase separation could be obtained, because dimethylaminoethyl acrylate and dimethylaminoethyl methacrylate are known to have substantial water solubilities.

TABLE 1

|  | Amine Reactant | Phase Separation | Reaction Rate at 60° C. |
|---|---|---|---|
| Ex. 4 | Dimethylaminoethyl acrylate | good | fast |
| Ex. 5 | Dimethylaminoethyl methacrylate | good | fast |
| C. Ex. 2 | Dimethylaminopropyl acrylate | poor (single phase) | very fast |
| C. Ex. 3 | Diethylaminoethyl methacrylate | (not determined) | very slow |
| C. Ex. 4 | Dimethylaminopropyl acrylamide | poor (single phase) | very fast |

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

All ranges disclosed herein are inclusive of the endpoints, and the endpoints are independently combinable with each other.

The use of the terms "a" and "an" and "the" and similar referents in the context of describing the invention (especially in the context of the following claims) are to be construed to cover both the singular and the plural, unless otherwise indicated herein or clearly contradicted by context. Further, it should further be noted that the terms "first," "second," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

The invention claimed is:

1. A process for producing an unsaturated quaternary ammonium salt, comprising:
    reacting methyl chloride in a first vessel with a stoichiometric excess of an unsaturated tertiary amine in the presence of water to form a reaction mixture comprising the unsaturated quaternary ammonium salt and residual unsaturated tertiary amine;
    transferring a portion of the reaction mixture to a second vessel;
    phase separating the portion of the reaction mixture in the second vessel to yield a first fraction comprising the unsaturated quaternary ammonium salt and water, and a second fraction comprising the residual unsaturated tertiary amine;
    withdrawing a portion of the first fraction from the second vessel to recover the quaternary ammonium salt product; and
    recycling a portion of the second fraction from the second vessel to the first vessel for use in said reacting methyl chloride with a stoichiometric excess of unsaturated tertiary amine;
    wherein the unsaturated tertiary amine has the formula

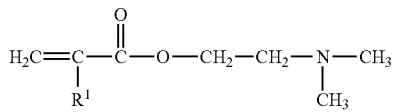

wherein $R^1$ is hydrogen or methyl; and
    wherein the unsaturated quaternary ammonium salt has the formula

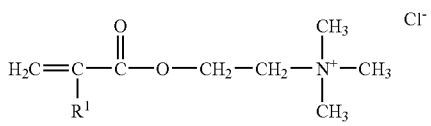

wherein $R^1$ is hydrogen or methyl.

2. The process of claim 1, operated continuously.

3. The process of claim 1, wherein the stoichiometric excess of the unsaturated tertiary amine corresponds to a molar ratio of unsaturated tertiary amine to methyl chloride of 1.05:1 to 5:1, as determined for inputs to the first vessel.

4. The process of claim 1, wherein the unsaturated tertiary amine is 2-(dimethylamino)ethyl acrylate.

5. The process of claim 1, wherein the unsaturated tertiary amine is 2-(dimethylamino)ethyl methacrylate.

6. The process of claim 1, wherein said reacting comprises continuously feeding to the first vessel 6 to 20 weight percent methyl chloride, 18 to 57 weight percent unsaturated tertiary amine, 6 to 19 weight percent water, and 3 to 70 weight percent of the recycled portion of the second fraction, wherein all weight percents are based on the total weight of inputs to the first vessel.

7. The process of claim 1, wherein said reacting is conducted with a first vessel residence time of 0.25 to 3 hours.

8. The process of claim 1, wherein said reacting is conducted at a total pressure of 100 to 800 kilopascals.

9. The process of claim 1, wherein said reacting methyl chloride with an unsaturated tertiary amine is conducted at a temperature of 30 to 90° C.

10. The process of claim 1, wherein said phase separating is conducted at a temperature of −5 to 15° C.

11. The process of claim 1, wherein the first fraction comprises at least 95 percent of the unsaturated quaternary ammonium salt in the second vessel, and the second fraction comprises at least 95 percent of the residual unsaturated tertiary amine in the second vessel.

12. The process of claim 1,
    wherein the stoichiometric excess of the unsaturated tertiary amine corresponds to a molar ratio of unsaturated tertiary amine to methyl chloride of 1.1:1 to 4:1, as determined for inputs to the first vessel;
    wherein said reacting comprises continuously feeding to the first vessel 6 to 20 weight percent methyl chloride, 18 to 57 weight percent unsaturated tertiary amine, 6 to 19 weight percent water, and 3 to 70 weight percent of the recycled portion of the second fraction,
    wherein all weight percents are based on the total weight of inputs to the first vessel;
    wherein said reacting is conducted with a first vessel residence time of 0.25 to 3 hours;
    wherein said reacting methyl chloride with an unsaturated tertiary amine is conducted at a temperature of 30 to 90° C.;
    wherein said reacting is conducted at a pressure of 150 to 600 kilopascals;
    wherein said separating is conducted at a temperature of −5 to 15° C.; and
    wherein the first fraction comprises at least 95 percent of the unsaturated quaternary ammonium salt in the second vessel, and the second fraction comprises at least 95 percent of the residual unsaturated tertiary amine in the second vessel.

* * * * *